US008563233B2

(12) United States Patent
Thatte

(10) Patent No.: US 8,563,233 B2
(45) Date of Patent: Oct. 22, 2013

(54) BLOOD SUBSTITUTE SOLUTION

(75) Inventor: Hemant Thatte, Medfield, MA (US)

(73) Assignees: President and Fellows of Harvard College, Cambridge, MA (US); The United States of America as Represented by the Department of Veterans Affairs, Washington, DC (US)

( * ) Notice: Subject to any disclaimer, the term of this patent is extended or adjusted under 35 U.S.C. 154(b) by 332 days.

(21) Appl. No.: 12/867,411

(22) PCT Filed: Feb. 10, 2009

(86) PCT No.: PCT/US2009/000831
§ 371 (c)(1),
(2), (4) Date: Dec. 16, 2010

(87) PCT Pub. No.: WO2009/105164
PCT Pub. Date: Aug. 27, 2009

(65) Prior Publication Data
US 2011/0091863 A1    Apr. 21, 2011

Related U.S. Application Data

(60) Provisional application No. 61/065,949, filed on Feb. 15, 2008.

(51) Int. Cl.
*A01N 1/00* (2006.01)

(52) U.S. Cl.
USPC ........................................................ 435/1.2

(58) Field of Classification Search
None
See application file for complete search history.

(56) References Cited

U.S. PATENT DOCUMENTS

| | | | |
|---|---|---|---|
| 4,256,834 | A | 3/1981 | Zuk et al. |
| 4,415,556 | A | 11/1983 | Bretschneider |
| 4,675,314 | A | 6/1987 | Strumia |
| 4,798,824 | A | 1/1989 | Belzer et al. |
| 4,879,283 | A | 11/1989 | Belzer et al. |
| 5,075,210 | A | 12/1991 | Wikman-Coffelt |
| 5,130,230 | A | 7/1992 | Segall et al. |
| 5,200,398 | A | 4/1993 | Strasberg et al. |
| 5,243,044 | A | 9/1993 | Dandliker et al. |
| 5,279,937 | A | 1/1994 | Rowe |
| 5,554,497 | A | 9/1996 | Raymond |
| 5,714,515 | A | 2/1998 | Bunger |
| 5,945,272 | A | 8/1999 | Segall et al. |
| 6,028,107 | A | 2/2000 | Waugh |
| 6,046,046 | A | 4/2000 | Hassanein |
| 6,492,103 | B1 | 12/2002 | Taylor |
| 6,521,248 | B1 | 2/2003 | Holloway et al. |
| 6,524,785 | B1 | 2/2003 | Cozzone et al. |
| 6,528,540 | B2 | 3/2003 | Liu et al. |
| 6,569,615 | B1 | 5/2003 | Thatte et al. |
| 6,680,305 | B1 | 1/2004 | Segall et al. |
| 6,994,954 | B2 | 2/2006 | Taylor |
| 7,198,254 | B2 | 4/2007 | Holloway et al. |
| 2002/0132220 | A1 | 9/2002 | Berens et al. |
| 2003/0124503 | A1 | 7/2003 | Olivencia-Yurvati et al. |
| 2004/0009894 | A1 | 1/2004 | Hobai et al. |
| 2004/0018245 | A1 | 1/2004 | Steen |
| 2004/0038192 | A1 | 2/2004 | Brasile |
| 2005/0136391 | A1 | 6/2005 | Steinhardt |
| 2005/0147958 | A1 | 7/2005 | Hassanein et al. |
| 2006/0154357 | A1* | 7/2006 | Hassanein et al. ......... 435/284.1 |
| 2006/0154359 | A1 | 7/2006 | Hassanein et al. |
| 2007/0098694 | A1 | 5/2007 | Khuri et al. |
| 2007/0254862 | A1 | 11/2007 | Antel et al. |
| 2012/0264103 | A1 | 10/2012 | Thatte et al. |
| 2012/0282591 | A1 | 11/2012 | Thatte et al. |

FOREIGN PATENT DOCUMENTS

| | | |
|---|---|---|
| CN | 1791341 A | 6/2006 |
| EP | 0199117 A2 | 10/1986 |
| EP | 1000541 A1 | 5/2000 |
| WO | WO-9211773 A1 | 7/1992 |
| WO | WO-0101774 A1 | 1/2001 |
| WO | WO-0130754 A2 | 5/2001 |
| WO | WO-0205870 A2 | 1/2002 |
| WO | WO-02102149 A1 | 12/2002 |
| WO | WO-2004084807 A2 | 10/2004 |
| WO | WO-2005103080 A2 | 11/2005 |
| WO | WO-2006065920 A1 | 6/2006 |
| WO | WO-2006133273 A2 | 12/2006 |
| WO | WO-2008016937 A2 | 2/2008 |

OTHER PUBLICATIONS

Oriyanhan, et al. "Taurine Prevents Myocardial Ischemia-reperfusion-induced Oxidative Stress and Apoptosis in Prolonged Hypothermic Rat Heart Preservation" Heart Vessels 20:278-285 (2005).
Abe, H., "Role of histidine-related compounds as intracellular proton buffering constituents in vertebrate muscle", *Biochem. (Mosc)*, 65:757-765 (2000).
Bae et al., "Effects of lacidipine on vascular responses in patients with coronary artery disease", *Int. J. Cardiol.*, 101(3):377-383 (2005).
Baptiste et al., "Effects of minocycline and tetracycline on retinal ganglion cell survival after axotomy", *Neuroscience*, 134:575-582 (2005).
Crespi, F., "Dihydropyridines, nitric oxide and vascular protection", *Curr. Vasc. Pharmacol.*, 3(2):195-205 (2005).

(Continued)

*Primary Examiner* — Sandra Saucier
(74) *Attorney, Agent, or Firm* — Mintz Levin Cohn Ferris Glovsky and Popeo, P.C.; Ingrid A. Beattle

(57) ABSTRACT

The invention relates generally to blood substitute solutions and methods for using blood substitute solutions. The solutions may be used in a variety of applications and are particularly suited for use in applications where at least a portion of a host's blood is replaced with a substitute solution.

7 Claims, No Drawings

(56) References Cited

OTHER PUBLICATIONS

Di et al., "Rapid Glucocorticoid-Mediated Endocannabinoid Release and Opposing Regulation of Glutamate and GABA Inputs to Hypothalamic Magnocellular Neurons", *Endocrin.*, 145(10):4292-4301 (2005).

Fernandez-Gomez et al., "Involvement of mitochondrial potential and calcium buffering capacity in minocycline cytoprotective actions", *Neuroscience*, 133(4):959-967 (2005).

Hoffman, et al., "Effect of Creatine and β-Alanine Supplementation on Performance and Endocrine Responses in Strength /Power Athtletes", *Int. J. Sport Nutr. Ecxer. Metab.*,16:430-446 (2006).

Hohmann et al., "An endocannabinoid mechanism for stress-induced analgesia", *Nature*, 435:1108-1112 (2005).

Kocak-Toker et al., "Peroxynitrite induced decrease in $Na^+$, $K^+$-ATPase activity is restored by taurine", *World J. Gastroenterol.*, 11(23):3554-3557 (2005).

Kurabayashi et al., "2-Arachidonoylglycerol increases in ischemia-reperfusion injury of the rat liver", *J. Invest. Surg.*, 18(1):25-31 (2005).

Loriette et al., "Dietary Casein Levels and Taurine Supplementation. Effects on Cysteine Dioxygenase and Cysteine Sulfinate Decarboxylase Activities and Taurine Concentration in Brain, Liver and Kidney of the Rat", *Nutr. Metab.*, 23(6):467-475 (1979).

Molchanova et al., "Mechanisms of enhanced taurine release under $Ca^{2+}$ depletion", *Neurochem. Int.*, 47:343-349 (2005).

Panikashvili et al., "$CB_1$ cannabinoid receptors are involved in neuroprotection via NF-kappa B inhibition", *J. Cereb, Blood Flow Metab.*, 25(4):477-484 (2005).

Tian et al., "The Conformation, Location, and Dynamic Properties of the Endocannabinoid Ligand Anandamide in a Membrane Bilayer", *J. Biol. Chem.*, 280(33):29788-29795 (2005).

Wang et al., "Minocycline inhibits LPS-induced retinal microglia activation", *Neurochem. Int.*, 47:152-158 (2005).

Zaliunas et al., "Effects of amlodipine and lacidipine on heart rate variability in hypertensive patients with stable angina pectoris and isolated left ventricular diastolic dysfunction," *Int., J. Cardiol.*, 101(3):347-353 (2005).

Zoeller et al., "Effects of creatine and beta-alanine on ventilatory and Lactate thresholds in men", *Amino Acids*, 33:505-510 (2006).

"Hanks' Balanced Salt Solutions (HBSS) (1)." *GIBCO BRL Catalogue & Reference Guide.* (1992):119.

Boehm et al. "Adenosine Cardioplegia: Reducing Reperfusion Injury of the Ischaemic Myocardiums?" *J. Mol. Cell. Cardio.* 22.S5(1990). (Abstract #P13).

Boku et al. "A Comparative Study of Cardiac Preservation with Celsior or University of Wisconsin Solution with or without Prior Administration of Cardioplegia." *J. Heart Lung Transplant.* 25(2006):219-225.

Ferrera et al. "Comparison of Different Techniques of Hypothermic Pig Heart Preservation." *Ann. Thorac. Surg.* 57(1994):1233-1239.

Hearse et al. "Creatine Phosphate and Protection Against Reperfusion-Induced Arrhymias in the Rat Heart." *Eur. J. Pharmacol.* 131. 1(1986):21-30.

Igarashi et al. "Calcium-Independent Activation of Endothelial Nitric Oxide Synthase by Ceramide." *PNAS.* 96.22(1999):12583-12588.

Ikeda et al. "Cardioprotective Effects of Citrulline in Ischemia/Reperfusion Injury Via a Non-Nitric Oxide-Mediated Mechanism." *Method. Find. Exp. Clin. Pharmacol.* 22.7(2000):563-571.

Lango et al. "Influence of L-carnitine and its Derivatives on Myocardial Metabolism and Function in Ischemic Heart Disease and During Cardiopulmonary Bypass." *Cardiovasc. Res.* 51.1(2001):21-29.

Maurer et al. "Comparison of UW and Collins Solution for Preservation of the Rat Heart." *Transplant. Pro.* 22.2(1990):548-550.

Michel. "Evaluation of a New Preservative Solution for Cardiac Graft During Hypothermia." *J. Heart Lung Transplant.* 19.11(2000):1089-1097.

Nakatsubo et al. "Direct Evidence of Nitric Oxide Production From Bovine Aortic Rndothelial Cells Using New Fluorescence Indicators: Diaminofluoresceins." *FEBS Lett.* 427.2(1998):263-266.

Oshima et al. "Long-Term Heart Preservation Using a New Portable Hypothermic Perfusion Apparatus." *J. Heart Lung Transplant.* 18.9(1999):852-861.

Puetz et al. "Effects of L-Carnitine-Hydrochloride in the Cold Ischemic Preservation of Fatty Liver Grafts." *Transplant. Proc.* 33(2001):2523-2524.

Southard et al. "Important Components of the UW Solution1,2." *Transplant.* 49.2(1990):251-257.

Swanson et al. "Improved Heart Preservation with UW Preservation Solution." *J. Heart Transplant.* 7(1988):456-467.

Thatte et al. "The Coronary Artery Bypass Conduit: I. Intraoperative Endothelial Injury and Its Implication on Graft Patency." *Ann. Thorac. Surg.* 72(2001):S2245-S2252.

\* cited by examiner

BLOOD SUBSTITUTE SOLUTION

RELATED APPLICATIONS

This application is a national stage application, filed under 35 U.S.C. §371, of International Application No. PCT/US2009/000831, filed Feb. 10, 2009, which claims the benefit of provisional application U.S. Ser. No. 61/065,949 filed Feb. 15, 2008, the contents of which are incorporated by reference in their entireties.

STATEMENT AS TO FEDERALLY SPONSORED RESEARCH

This invention was made with Government support under Office of Naval Research award N00014-06-1-0100. The Government has certain rights in the invention.

FIELD OF THE INVENTION

The invention relates generally to blood substitute solutions and methods for using blood substitute solutions.

BACKGROUND OF THE INVENTION

For a variety of reasons, it is not always practical to transfuse a patient with donated blood. In these situations, use of a red blood cell substitute is necessary. Although solutions derived from mammalian blood have been used with success, because such solutions are derived from natural blood, they can contain various pathogenic substances, such as viral pathogens including HIV, Hepatitis B, and other pathogens, e.g. prions such as those associated with Cruetzfeldt-Jakob disease, and the like. Accordingly, there is interest in the development of new physiologically acceptable solutions that are suitable for use as blood substitutes, which are prepared from non-blood derived components.

SUMMARY OF THE INVENTION

The invention relates to blood substitute solutions. The solutions may be used in a variety of applications and are particularly suited for use in applications where at least a portion of a host's blood is replaced with a substitute solution. In one aspect, the solutions of the invention prevent against acidosis. In another aspect, the solutions of the invention hydrate the body.

The invention provides a physiologically acceptable solution suitable for administration as a blood substitute comprising a physiological salt solution, pyruvate, and beta-alanine. Optionally, the solution comprises a physiological salt solution, pyruvate, beta-alanine, and one or more ingredients selected from the group consisting of D-glucose, 3-beta hydroxy butyrate, alpha-ketoglutarate, acetoacetate, and an intralipid solution.

Optionally, the invention provides a physiologically acceptable solution suitable for administration as a blood substitute comprising a physiological salt solution, beta-alanine, pyruvate, and 3-beta hydroxy butyrate.

In yet another aspect, the invention provides a physiologically acceptable solution suitable for administration as a blood substitute comprising a physiological salt solution, beta-alanine, pyruvate, and alpha-ketoglutarate.

The invention also provides a physiologically acceptable aqueous solution suitable for administration as a blood substitute comprising a physiological salt solution, beta-alanine, pyruvate, and acetoacetate.

Also provided is a physiologically acceptable aqueous solution suitable for administration as a blood substitute comprising a physiological salt solution, beta-alanine, pyruvate, and an intralipid solution.

The invention provides a physiologically acceptable solution suitable for administration as a blood substitute comprising a physiological salt solution further comprising at least one, at least two, or at least three of a composition selected from the group consisting of an energy source, a reagent that buffers intracellular acidity, and an antioxidant.

The invention also provides a physiologically acceptable solution suitable for administration as a blood substitute comprising a physiological salt solution and an energy source. In one aspect, the energy source is pyruvate. In another aspect, the energy source is 3-beta hydroxy butyrate. In yet another aspect, the energy source is alpha-ketoglutarate. Optionally, the energy source is acetoacetate. Alternatively, the energy source is intralipid solution.

Optionally, the solution contains D-glucose. The presence of D-glucose in the solution is at the discretion of the surgeon. In one aspect, if the patient has diabetes, D-glucose is not included in the blood substitute solution. Alternatively, if the patient does not have diabetes, D-glucose is included in the blood substitute solution.

The invention also provides a physiologically acceptable solution suitable for administration as a blood substitute comprising a physiological salt solution and a reagent that buffers intracellular acidity. Preferably, the reagent that buffers intracellular acidity is beta-alanine.

In another aspect, the invention provides a physiologically acceptable solution suitable for administration as a blood substitute comprising a physiological salt solution and an antioxidant. Preferably, the antioxidant is taurine.

The invention also provides a composition comprising:

| | |
|---|---|
| 0.01-3.0 L | Distilled water |
| 0.1-0.5 gm/L | Calcium chloride |
| 0.1-0.5 gm/L | Potassium chloride |
| 0.01-0.25 gm/L | Potassium phosphate (monobasic) |
| 0.05-0.5 gm/L | Magnesium chloride (hexahydrate) |
| 0.05-0.5 gm/L | Magnesium sulfate (heptahydrate) |
| 5-10 gm/L | Sodium chloride |
| 0.25-0.75 gm/L | Sodium bicarbonate |
| 0.01-0.1 gm/L | Sodium phosphate (dibasic; hepatahydrate) |
| 0.1-1.0 gm/L | Pyruvate |
| 0.1-1.0 gm/L | Glutathione (reduced) |
| 0.05-0.5 gm/L | Ascorbic acid |
| 0.5-2.5 gm/L | L-Arginine |
| 0.1-1.0 gm/L | L-Taurine |
| 0.1-1.0 gm/L | Beta-alanine |
| 0.1-0.5 gm/L | Creatine monohydrate |
| 0.5-1.5 gm/L | L-Carnitine |
| 1.0-5.0 gm/L | L-Carnosine (10 mM) |

Tris-hydroxymethyl aminomethane (THAM) is used to adjust pH. Alpha-ketoglutarate, 3-beta hydroxy butyrate, acetoacetate, and/or intralipid solution may be present or absent.

Optionally, the solution further comprises a composition selected from the group consisting of D-glucose, 3-beta hydroxy butyrate, alpha-ketoglutarate, acetoacetate, and intralipid solution.

Kits comprising the solutions described herein are also provided by the invention.

In one aspect, the solution comprises water clusters in a nanometer range of size. Optionally, the solution of the invention is nano-sized to increase the efficiency of traversing the cellular membrane. Nano-sizing refers to the reduction of the particle size to the sub-micron range, with the final particle size typically being 1-10 ηm. The reduction of particle size leads to a significant increase in the efficiency of the solution in traversing the cellular membrane. In one aspect, the efficiency is increased such that at least 20%, at least 25%, at least 50%, at least 75%, or at least 100% of the solution traverses the cellular membrane.

The invention provides for nano-sizing the solution of the invention prior to use in the methods described herein. Alternatively, the invention provides for nano-sizing the water prior to adding the other compounds/reagents of the solution. In yet another aspect, the invention provides for nano-sizing the water and nano-sizing each compound/reagent of the solution separately prior to mixing in solution.

In one aspect, the composition comprises water packets or water clusters in a nanometer range of size. Optionally, the water packets or water clusters are 1-10 ηm, 1-25 ηm, 25-50 ηm, 50-75 ηm, 75-100 ηm, 100-200 ηm, 200-500 ηm, or 500-999 ηm.

In another aspect, the solutions presented are mixed with blood prior to use. Optionally, the blood:solution ratio is 5:1, 4:1, 3:1, 2:1 or 1:1. Alternatively, the blood:solution ratio is 1:2, 1:3, 1:4, or 1:5.

In one aspect, the ingredients of the invention are provided in aqueous solution. Alternatively, the ingredients of the invention are in powder form and reconstituted prior to use. Preferably, the ingredients are reconstituted in water.

The invention provides blood substitute solutions and compositions that are useful in any situation where an I.V. drip is employed. The blood substitute solutions of the invention are used during delivery and surgery. In another aspect, the solutions of the invention are used as a blood substitute in a patient that has experienced severe trauma, bleeding, and the like. In another aspect, the solutions of the invention are used as a blood substitute in dehydrated patients. In yet another aspect, the solutions of the invention are used on the battlefield as a resuscitation fluid or for trauma application. The blood substitute solutions of the invention protect against acidosis and hydrate the body.

Cited publications are incorporated herein by reference. Both the foregoing general description and the following detailed description and examples are exemplary and explanatory only and are not restrictive of the invention as claimed.

DETAILED DESCRIPTION OF THE INVENTION

Physiologically acceptable blood substitute solutions find use in a variety of different applications in the medical, biomedical research and related fields. For example, physiologically acceptable solutions find use as blood substitutes in surgical applications which require the replacement of significant amounts of blood volume. Such applications include treatments for blood lost during surgery or trauma, or when a tissue, organ, group of organs or an entire subject needs to be maintained at a hypothermic or frozen state. Such applications also include applications in which a patient's blood is flowed through an external device, such as a cardiopulmonary bypass machine, where the extra circulatory volume space resulting from attachment of the patient's circulatory system to the device must be filled with a compatible blood substitute, i.e., blood volume expander.

Physiologically acceptable solutions suitable for use as blood substitutes must be able to mix freely with blood without unacceptably compromising its components, such as creating precipitates which significantly block flow in small vessels, destroying an unacceptable portion of its formed elements (cells, platelets), introducing agents or creating water, ionic or molecular imbalances destructive to body cells and tissues, or causing harmful physiologic activities such as inappropriate acceleration or inhibition of heartbeat, nerve conduction or muscle contraction, and the like.

The solutions of the invention are used in a variety of surgical settings and procedures. It is useful in delicate neurosurgery where clear surgical fields are imperative and reduced central nervous system activity is desirable and achieved by performing the procedure on a patient whose core temperature and/or cerebral temperature has been substantially reduced.

Optionally, the solution according to the invention is administered using an intravenous line (when the subject is at normal temperature) or to a chilled subject using a pumped circulating device such as a centrifugal pump, roller pump, peristaltic pump or other known and available circulatory pump. The circulating device is connected to the subject via cannulae inserted surgically into appropriate veins and arteries. When the solution is administered to a chilled subject, it is generally administered via an arterial cannula and removed from the subject via a venous cannula and discarded, stored or circulated.

In one aspect, the solution may be used to maintain a subject which has lost a significant amount of blood, e.g., at least 5%, at least 10%, at least 20%, at least 50%, at least 75% or at least 98% of its blood, at normal body temperatures in a pressurized environment at increased oxygen concentration above atmospheric oxygen tension up to 100% oxygen. Optionally, the subject is maintained in a high oxygen concentration, either continuously or periodically, until enough blood components can be synthesized by the subject to support life at atmospheric pressure and oxygen concentration.

Alternatively, the solution according to the invention is used to maintain a subject at temperatures lower than normal body temperature and at a reduced rate of metabolism after traumatic life-threatening injury until appropriate supportive or corrective surgical procedures can be performed. In addition, the solution is used to maintain a patient having a rare blood or tissue type until an appropriate matching donor can be found and replacement blood units or other organ can be obtained.

In one aspect, the blood substitute solutions and compositions comprise a physiological salt solution and a substrate for the production of ATP. Optionally, the substrate for the production of ATP is phosphocreatine, creatine ethyl ester, dicreatine malate, creatine gluconate, fructose, sucrose, ribose, hexose or pentose. Alternatively, the substrate for the production of ATP is creatine orotate, creatine monohydrate, adenosine, or dextrose/glucose.

In another aspect, the blood substitute solutions and compositions comprise a physiological salt solution and a reagent that buffers intracellular acidity. In one aspect, the reagent that buffers intracellular acidity is histidine, glutamine, tryptophan, lysine, or L-taurine. Acidity is also buffered by sodium bicarbonate, Tris-hydroxymethyl aminomethane (THAM), L-carnosine (intracellular acidity), and Beta-alanine. L-carnitine facilitates a decrease in myocardial lactate production, hence reducing acidity. Alternatively, a reagent that buffers intracellular acidity is creatine orotate via facilitated synthesis of carnosine. Creatine monohydrate buffers acidity by increasing energy production and decreasing lactate accumulation.

Optionally, the blood substitute solutions and compositions comprise a physiological salt and a reagent that quenches reactive oxygen species. In one aspect, the reagent that quenches reactive oxygen species is dithiothreitol (DTT), beta-Mercaptoethanol, Acetylcysteine, Alpha lipoic acid, Taurine, Reserveratrol, Lutein, Selenium, Methionine, or Tocopherols/Vitamin E.

The blood substitute solutions and compositions prevent ischemic injury. This function is mediated by ascorbic acid, glutathione (reducing agent), carnitine (by preventing accumulation of long chain acyl-CoA that leads to generation of free radicals-ischemic-reperfusion injury), carnosine and alpha lipoic acid, which are free radical (hydroxyl radical, singlet oxygen, peroxyl radical and superoxide) scavengers.

The blood substitute solutions and compositions contain beta alanine. Beta alanine is an amino acid, which is an agonist next in activity to the cognate ligant glycine, for strychnine-sensitive inhibitory glycine receptors (GlyRs) (the agonist order: glycine>>b-alanine>taurine>>1-alanine, 1-serine>proline). Beta alanine buffers intracellular acidity and pH, improves muscle contraction and increases aerobic threshold.

The intracellular non-bicarbonate buffering capacity of vertebrate muscle is mainly supported by the imidazole groups of histidine residues in proteins, free L-histidine in some fish species, and histidine-containing dipeptides such as carnosine, anserine, and balenine (ophidine) (Abe H, 2000 *Biochemistry (Mosc)*, 65(7):757-65). Results have demonstrated the efficacy of creatine and beta-alanine on strength performance in athletes (Hoffman J et al., 2006 *Int J Sport Nutr Exerc Metab,* 16(4):430-46).

In one aspect, the blood substitute solutions and compositions contain L-taurine. L-taurine is a sulfur-containing beta amino acid, which has been implicated in a wide array of physiological phenomena including regulation of heartbeat, osmoregulation, membrane stabilization, preservation of aerobic metabolism, prevention of lactic acidosis, inhibitory neurotransmission, long-term potentiation in the striatum/hippocampus, feedback inhibition of neutrophil/macrophage respiratory bursts, adipose tissue regulation, and calcium homeostasis. Taurine also acts as an antioxidant, and is an endogenous agonist of glycine receptor. An acceptable concentration of taurine in the blood substitute solutions and compositions is 10 mM.

The sulfur-containing amino acid taurine is an inhibitory neuromodulator in the brain of mammals, as well as a key substance in the regulation of cell volumes. The effect of $Ca^{2+}$ on extracellular taurine concentrations is of special interest in the context of the regulatory mechanisms of taurine release. Data imply the involvement of both decreased influx of $Ca^{2+}$ and increased non-specific influx of $Na^+$ through voltage-sensitive calcium channels in the regulation of transporter-mediated taurine release in $Ca^{2+}$ depletion (Molchanova S M et al., 2005 *Neurochem Int,* 47(5):343-9). Moreover, Taurine is observed to act as an antioxidant of peroxynitrite ($ONOO^-$) to decrease lipid peroxidation and thus affect liver plasma membrane $Na^+$, K+-ATPase by restoring its activity (Kocak-Toker N, et al., 2005 *World J Gastroenterol,* 11(23):3554-7).

In one aspect, the blood substitute solutions of the invention potassium chloride. The potassium concentration in the solution is varied at the surgeon's discretion over a desired range without varying the dilution of the blood substitute solution or the concentration of other ingredients. Alternatively, the potassium and/or other concentrations are varied, while independently varying the degree of dilution and the total flow of blood substitute solution to the patient's heart. Varying the potassium concentration in the solution allows the perfusionist to minimize the total amount of potassium added to the patient's blood during an operation. A high initial potassium concentration can rapidly arrest the heart and a lower potassium concentration can maintain arrest. The amount of potassium is adjusted to compensate for the increase in the patient's serum potassium level throughout the course of the operation. Optionally, the potassium concentration of the solution is adjusted in the event of a reoccurrence of heart activity during surgery.

The invention also provides a blood substitute solution comprising a physiological salt solution and an energy source. Optionally, the blood substitute energy source is pyruvate, 3 beta-hydroxy butyrate, alpha-ketoglutarate, acetoacetate, intralipid solution or glucose. In patients with brain injury, diabetes, or in other cases where glucose cannot be utilized, the solution comprises 3 beta-hydroxy butyrate, alpha-ketoglutarate, acetoacetate, and/or intralipid solution. Alternatively, the solution is glucose free or contains dextrose, fructose, or other forms of sugar, e.g., maltodextrin.

Optionally, the blood substitute solution contains D-glucose. The presence of D-glucose in the blood substitute solution is at the discretion of the surgeon. In one aspect, if the patient has diabetes, D-glucose is not included in the blood substitute solution. Alternatively, if the patient does not have diabetes, D-glucose is included in the blood substitute solution. D-glucose acts as a vasodilator and a sleep-inducing agent.

In one aspect, the blood substitute solutions of the invention comprise pyruvic acid ($CH_3COCO_2H$), an alpha-keto acid. The carboxylate anion of pyruvic acid is known as pyruvate. Pyruvate is the output of the anaerobic metabolism of glucose known as glycolysis. One molecule of glucose breaks down into two molecules of pyruvate, which are then used to provide further energy. Pyruvate is converted into acetyl-coenzyme A, which is the main input for the Krebs cycle. Pyruvate is also converted to oxaloacetate by an anaplerotic reaction which replenishes Krebs cycle intermediates; alternatively, the oxaloacetate is used for gluconeogenesis. Pyruvate also enters the TCA cycle for continuous generation of ATP.

In humans, 3 beta-hydroxy butyrate is synthesized in the liver from acetyl-CoA, and can be used as an energy source by the brain when blood glucose is low. Alpha-ketoglutaric acid is one of two ketone derivatives of glutaric acid. Its anion, alpha-ketoglutarate (also called oxo-glutarate) is the keto acid produced by de-amination of glutamate, and is an intermediate in the Krebs cycle.

The solutions of the invention are used in place of Lactated Ringer's solution, a solution that is isotonic with blood and intended for intravenous administration. Alternatively, the solutions of the invention are used in place of normal saline. In one aspect, the solutions of the invention are used for fluid resuscitation after a blood loss due to trauma, surgery, or a burn injury. The solutions of the invention prevent acidosis, which is a chemical imbalance that occurs with acute fluid loss or renal failure.

The invention provides blood substitute solutions and compositions that are useful in any situation where an I.V. drip is employed. The blood substitute solutions of the invention are used during delivery and surgery. In another aspect, the solutions of the invention are used as a blood substitute in a patient that has experienced severe trauma, bleeding, and the like. In another aspect, the solutions of the invention are used as a blood substitute in dehydrated patients. In another aspect, the solutions of the invention are used on the battlefield as a resuscitation fluid or for trauma application. For battlefield or trauma application, 1-100 mM alpha-ketoglutarate is added.

In one aspect, the ingredients of the invention are provided in aqueous solution. Alternatively, the ingredients of the invention are in powder form and reconstituted prior to use. Preferably, the ingredients are reconstituted in water.

In another aspect, the solution of the invention is a volume expander or a pump prime solution. In one aspect, the solution comprises calcium chloride, potassium phosphate, magnesium chloride, magnesium sulfate, sodium chloride, sodium bicarbonate, sodium phosphate, pyruvate, glutathione, ascorbic acid, L-arginine, L-taurine, beta-alanine, L-carnosine, creatine monohydrate, and L-carnitine. Optionally, the solution also comprises one or more of D-glucose, 3-beta hydroxy butyrate, alpha-ketoglutarate, acetoacetate, and intralipid solution. Alternatively, the solution comprises dextrose, fructose, or malodextrin.

The pH of the solution is adjusted to about 6.8 to about 8.0; or about 7.2 to about 7.6. More preferably, the pH is adjusted to about 7.4 using sodium bicarbonate or THAM (tromethamine; tris-hydroxymethyl aminomethane), and maintained at 21° C. The osmolarity is maintained at 290-300 mOsM. Preferably, the composition includes the following compounds and concentrations:

| | |
|---|---|
| Distilled water | 1.00 L |
| Calcium chloride (1.3 mM) | 0.191 gm/L |
| Potassium chloride (4.0 mM) | 0.298 gm/L |
| Potassium phosphate (monobasic; 0.5 mM) | 0.068 gm/L |
| Magnesium chloride (hexahydrate; 0.5 mM) | 0.101 gm/L |
| Magnesium sulfate (heptahydrate; 0.5 mM) | 0.123 gm/L |
| Sodium chloride (130 mM) | 7.597 gm/L |
| Sodium bicarbonate (5.0 mM) | 0.420 gm/L |
| Sodium phosphate (dibasic; hepatahydrate; 0.19 mM) | 0.050 gm/L |
| D-Glucose (11 mM) | 1.982 gm/L * |
| Pyruvate (5 mM) | 0.631 gm/L |
| Glutathione (reduced; 1.5 mM) | 0.461 gm/L |
| Ascorbic acid (1 mM) | 0.176 gm/L |
| L-Arginine (5 mM) | 1.073 gm/L |
| L-Taurine (5 mM) | 0.625 gm/L |
| Beta-alanine (5 mM) | 0.500 gm/L |
| Creatine monohydrate (2 mM) | 0.298 gm/L |
| L-Carnitine (5 mM) | 1.00 gm/L |
| L-Carnosine (10 mM) | 2.260 gm/L |
| 3-beta hydroxy butyrate (10-100 mM) | * |
| Alpha-ketoglutarate (10-30 mM) | * |
| Acetoacetate (10-30 mM) | * |
| Intralipid solution (10%) | * |

The designation "*" denotes that D-Glucose, alpha-ketoglutarate, 3-beta hydroxy butyrate, acetoacetate, and/or intralipid solution may be present or absent in the solution based on the discretion of the surgeon or needs of the patient. In patients with brain injury, diabetes, or in other cases where glucose cannot be utilized, the solution comprises 3 beta-hydroxy butyrate, alpha-ketoglutarate, acetoacetate, and/or intralipid solution. Alternatively, the solution is glucose free or contains dextrose, fructose, or other forms of sugar, e.g., maltodextrin.

A preferred blood substitute solution includes amounts of the compounds in the following ranges to achieve a desired ratio of compositions:

| | |
|---|---|
| Distilled water | 0.01-3.0 L |
| Calcium chloride (1.3 mM) | 0.1-0.5 gm/L |
| Potassium chloride (4.0 mM) | 0.1-0.5 gm/L |
| Potassium phosphate (monobasic; 0.5 mM) | 0.01-0.25 gm/L |
| Magnesium chloride (hexahydrate; 0.5 mM) | 0.05-0.5 gm/L |
| Magnesium sulfate (heptahydrate; 0.5 mM) | 0.05-0.5 gm/L |
| Sodium chloride (130 mM) | 5-10 gm/L |
| Sodium bicarbonate (5.0 mM) | 0.25-0.75 gm/L |
| Sodium phosphate (dibasic; hepatahydrate; 0.19 mM) | 0.01-0.1 gm/L |
| D-Glucose (11 mM) | 0.5-2.5 gm/L * |
| Pyruvate (5 mM) | 0.1-1.0 gm/L |
| Glutathione (reduced; 1.5 mM) | 0.1-1.0 gm/L |
| Ascorbic acid (1 mM) | 0.05-0.5 gm/L |
| L-Arginine (5 mM) | 0.5-2.5 gm/L |
| L-Taurine (5 mM) | 0.1-1.0 gm/L |
| Beta-alanine (5 mM) | 0.1-1.0 gm/L |
| Creatine monohydrate (2 mM) | 0.1-0.5 gm/L |
| L-Carnitine (5 mM) | 0.5-1.5 gm/L |
| L-Carnosine (10 mM) | 1.0-5.0 gm/L |
| 3-beta hydroxy butyrate (10-100 mM) | * |
| Alpha-ketoglutarate (10-30 mM) | * |
| Acetoacetate (10-30 mM) | * |
| Intralipid solution (10%) | * |

The designation "*" denotes that D-Glucose, alpha-ketoglutarate, 3-beta hydroxy butyrate, acetoacetate, and/or intralipid solution may be present or absent in the solution based on the discretion of the surgeon or needs of the patient. In patients with brain injury, diabetes, or in other cases where glucose cannot be utilized, the solution comprises 3 beta-hydroxy butyrate, alpha-ketoglutarate, acetoacetate, and/or intralipid solution. Alternatively, the solution is glucose free or contains dextrose, fructose, or other forms of sugar, e.g., maltodextrin.

The pH is adjusted to about 6.8 to about 8.0; or about 7.2 to about 7.6. Preferably, the pH is adjusted to about 7.4 using THAM, and maintained at 21° C. The osmolarity is maintained at 290-300 mOsM.

The compositions for making the blood substitute solutions are optionally packaged in a kit with the ingredients/amounts listed below or multiples thereof, i.e., scaled up to make 2, 3, 5, 10, 20 times the amount of solution. An exemplary kit contains:

| | |
|---|---|
| Distilled water | 1.00 L |
| Calcium chloride (1.3 mM) | 0.1-0.5 gm/L |
| Potassium chloride (4.0 mM) | 0.1-0.5 gm/L |
| Potassium phosphate (monobasic; 0.5 mM) | 0.01-0.25 gm/L |
| Magnesium chloride (hexahydrate; 0.5 mM) | 0.05-0.5 gm/L |
| Magnesium sulfate (heptahydrate; 0.5 mM) | 0.05-0.5 gm/L |
| Sodium chloride (130 mM) | 5-10 gm/L |
| Sodium bicarbonate (5.0 mM) | 0.25-0.75 gm/L |
| Sodium phosphate (dibasic; hepatahydrate; 0.19 mM) | 0.01-0.1 gm/L |
| D-Glucose (11 mM) | 0.5-2.5 gm/L * |
| Pyruvate (5 mM) | 0.1-1.0 gm/L |
| Glutathione (reduced; 1.5 mM) | 0.1-1.0 gm/L |
| Ascorbic acid (1 mM) | 0.05-0.5 gm/L |
| L-Arginine (5 mM) | 0.5-2.5 gm/L |
| L-Taurine (5 mM) | 0.1-1.0 gm/L |
| Beta-alanine (5 mM) | 0.1-1.0 gm/L |
| Creatine monohydrate (2 mM) | 0.1-0.5 gm/L |
| L-Carnitine (5 mM) | 0.5-1.5 gm/L |
| L-Carnosine (10 mM) | 1.0-5.0 gm/L |
| 3-beta hydroxy butyrate (10-100 mM) | * |
| Alpha-ketoglutarate (10-30 mM) | * |
| Acetoacetate (10-30 mM) | * |
| Intralipid solution (10%) | * |

The designation "*" denotes that D-Glucose, alpha-ketoglutarate, 3-beta hydroxy butyrate, acetoacetate, and/or intralipid solution may be present or absent in the solution based on the discretion of the surgeon or needs of the patient. In patients with brain injury, diabetes, or in other cases where glucose cannot be utilized, the solution comprises 3 beta-hydroxy butyrate, alpha-ketoglutarate, acetoacetate, and/or intralipid solution. Alternatively, the solution is glucose free or contains dextrose, fructose, or other forms of sugar, e.g., maltodextrin.

The pH is adjusted to about 6.8 to about 8.0; or about 7.2 to about 7.6. Preferably, the pH is adjusted to about 7.4 using THAM, and maintained at 21° C. The osmolarity is maintained at 290-300 mOsM.

These ingredients packaged together with instructions for use and are mixed in 0.01-2.0 L of distilled water. The kit is packaged or sold without the sterile water component. For example, the kit contains:

| | |
|---|---|
| Distilled water | 1.00 L |
| Calcium chloride (1.3 mM) | 0.191 gm/L |
| Potassium chloride (4.0 mM) | 0.298 gm/L |
| Potassium phosphate (monobasic; 0.5 mM) | 0.068 gm/L |
| Magnesium chloride (hexahydrate; 0.5 mM) | 0.101 gm/L |
| Magnesium sulfate (heptahydrate; 0.5 mM) | 0.123 gm/L |
| Sodium chloride (130 mM) | 7.597 gm/L |
| Sodium bicarbonate (5.0 mM) | 0.420 gm/L |
| Sodium phosphate (dibasic; hepatahydrate; 0.19 mM) | 0.050 gm/L |
| D-Glucose (11 mM) | 1.982 gm/L * |
| Pyruvate (5 mM) | 0.631 gm/L |
| Glutathione (reduced; 1.5 mM) | 0.461 gm/L |
| Ascorbic acid (1 mM) | 0.176 gm/L |
| L-Arginine (5 mM) | 1.073 gm/L |
| L-Taurine (5 mM) | 0.625 gm/L |
| Beta-alanine (5 mM) | 0.500 gm/L |
| Creatine monohydrate (2 mM) | 0.298 gm/L |
| L-Carnitine (5 mM) | 1.00 gm/L |
| L-Carnosine (10 mM) | 2.260 gm/L |
| 3-beta hydorxy butyrate (10-100 mM) | * |
| Alpha-ketoglutarate (10-30 mM) | * |
| Acetoacetate (10-30 mM) | * |
| Intralipid solution (10%) | * |

The designation "*" denotes that D-Glucose, alpha-ketoglutarate, 3-beta hydroxy butyrate, acetoacetate, and/or intralipid solution may be present or absent in the solution based on the discretion of the surgeon or needs of the patient. In patients with brain injury, diabetes, or in other cases where glucose cannot be utilized, the solution comprises 3 beta-hydroxy butyrate, alpha-ketoglutarate, acetoacetate, and/or intralipid solution. Alternatively, the solution is glucose free or contains dextrose, fructose, or other forms of sugar, e.g., maltodextrin.

The pH is adjusted to about 6.8 to about 8.0; or about 7.2 to about 7.6. Preferably, the pH is adjusted to about 7.4 using THAM, and maintained at 21° C. The osmolarity is maintained at 290-300 mOsM.

Optionally, the solution is nano-sized to increase the efficiency of the solution traversing the cellular membrane by any method known in the art, including the method described in U.S. Pat. Nos. 6,521,248 and 7,198,254, which are incorporated herein by reference in their entireties. Nano-sizing refers to the reduction of the particle size to the sub-micron range, with the final particle size typically being 1-10 ηm. The reduction of particle size leads to a significant increase in the efficiency of the solution in traversing the cellular membrane. In one aspect, the efficiency is increased such that at least 20%, at least 25%, at least 50%, at least 75%, or at least 100% of the solution traverses the cellular membrane.

The invention provides for nano-sizing for the solution of the invention prior to use in the methods described herein. Alternatively, the invention provides for nano-sizing the water prior to adding the other compounds/reagents of the solution. In yet another aspect, the invention provides for nano-sizing the water and nano-sizing each compound/reagent of the solution separately prior to mixing in solution.

In one aspect, the composition comprises water packets or water clusters in a nanometer range of size. Optionally, the water packets or water clusters are 1-10 ηm, 1-25 ηm, 25-50 ηm, 50-75 ηm, 75-100 ηm, 100-200 ηm, 200-500 ηm, or 500-999 ηm.

In another aspect, the solutions presented are mixed with blood prior to use. Optionally, the blood:solution ratio is 5:1, 4:1, 3:1, 2:1 or 1:1. Alternatively, the blood:solution ratio is 1:2, 1:3, 1:4, or 1:5.

Priming the Cardiopulmonary Bypass Circuit

The priming of the extracorporeal circuit is of particular importance in cardiac surgery. When cardiopulmonary bypass is instituted in the patient, the composition and volume of the priming solution determines the composition of the circulating blood. Although much variation exists, the use of priming solution composed of a pH balanced crystalloid base is preferred. The crystalloid base is similar in electrolyte content and osmolarity to plasma. These solutions that frequently contain metabolically active substrates such as HVA, Plasmalyte A, Normosol R, and Lactated Ringer's, are commonly used base priming solutions. Each oxygenator—tubing system will have a minimum safe priming volume, that is, one that will allow adequate flow rates without undue risk of air embolization.

The base priming solution for perfusion practice is pH balanced Harvard Veteran Affairs (HVA) solution. The main reason for priming the cpb circuit is so that there is absolutely no air in the system and to minimize the blood to gas interface and more importantly the introduction of air embolus to the patient. Aside from the issue of air embolization, priming the bypass circuit creates a layer between the blood and circuit material. This technique allows for minimizing the stimulation of the inflammation response, compliment, leukocyte, and platelet activation as well as disturbances in the hemostatic system.

A quick prime line connected to the venous reservoir is used to introduce the balanced crystalloid solution into circuit. The circuit that consists of the venous reservoir, tubing, centrifugal pump, heat exchanger, oxygenator, arterial filter and any part of the bypass circuit that comes in contact with the blood is primed in a way that air is displaced by the fluid until there is no air in the system. The circuit is then connected to the arterial and venous parts of the patient and bypass is initiated. The amount of priming solution is minimized without altering integrity of the circuit by using retrograde autologous priming (RAP) methods. Decreasing the prime volume allows to minimize the effects of excessive hemodilution.

TABLE 1

Target values for blood composition during cardiopulmonary bypass

| Component | Target values |
|---|---|
| pH | 7.35-7.45 |
| PO2 | 150 ± 50 mmHg |
| PCO2 | 40 ± 5 mmHg |
| Na | <140 mEq |
| K | 4.0 ± 0.5 mEq |
| Ca(i) | <0.8 mmol |
| Glucose | 50-100 mg/dl |

TABLE 1-continued

Target values for blood composition during cardiopulmonary bypass

| Component | Target values |
| --- | --- |
| Hematocrit | >25 |
| Oncotic pressure | 13-16 mmHg |
| Osmotic pressure | 300-320 mOsm/L |

What is claimed is:

1. A physiologically acceptable solution suitable for administration as a blood substitute, wherein said composition comprises:
    0.01-3.0 L distilled water
    0.1-0.5 gm/L calcium chloride
    0.1-0.5 gm/L potassium chloride
    0.01-0.25 gm/L potassium phosphate
    0.05-0.5 gm/L magnesium chloride
    0.05-0.5 gm/L magnesium sulfate
    5-10 gm/L sodium chloride
    0.25-0.75 gm/L sodium bicarbonate
    0.01-0.1 gm/L sodium phosphate
    0.1-1.0 gm/L pyruvate
    0.1-1.0 gm/L glutathione
    0.05-0.5 gm/L ascorbic acid
    0.5-2.5 gm/L L-Arginine
    0.1-1.0 gm/L L-Taurine
    0.1-1.0 gm/L Beta-alanine
    0.1-0.5 gm/L creatine monohydrate
    0.5-1.5 gm/L L-Carnitine
    1.0-5.0 gm/L L-Carnosine.

2. The solution of claim 1, wherein said solution further comprises D-glucose.

3. The solution of claim 1, wherein said solution further comprises 3-beta hydroxy butyrate.

4. The solution of claim 1, wherein said solution further comprises alpha-ketoglutarate.

5. The solution of claim 1, wherein said solution further comprises acetoacetate.

6. The solution of claim 1, wherein said solution further comprises and intralipid solution.

7. A physiologically acceptable solution suitable for administration as a blood substitute, wherein said composition comprises:
    Calcium chloride (1.3 mM)
    Potassium chloride (4.0 mM)
    Potassium phosphate (monobasic; 0.5 mM)
    Magnesium chloride (hexahydrate; 0.5 mM)
    Magnesium sulfate (heptahydrate; 0.5 mM)
    Sodium chloride (130 mM)
    Sodium bicarbonate (5.0 mM)
    Sodium phosphate (dibasic; hepatahydrate; 0.19 mM)
    Pyruvate (5 mM)
    Glutathione (reduced; 1.5 mM)
    Ascorbic acid (1 mM)
    L-Arginine (5 mM)
    L-Taurine (5 mM)
    Beta-alanine (5 mM)
    Creatine monohydrate (2 mM)
    L-Carnitine (5 mM)
    L-Carnosine (10 mM).

* * * * *